United States Patent [19]

Bratthall

[11] Patent Number: 5,374,538
[45] Date of Patent: Dec. 20, 1994

[54] METHOD AND KIT FOR DETECTION OR QUANTIFICATION OF STREPTOCOCCUS MUTANS AND STREPTOCOCCUS SOBRINUS

[75] Inventor: Douglas Bratthall, Malmo, Sweden
[73] Assignee: Orion-Yhtyma Oy, Expoo, Finland
[21] Appl. No.: 117,490
[22] Filed: Sep. 7, 1993

Related U.S. Application Data

[63] Continuation of Ser. No. 317,624, Mar. 1, 1989, abandoned.
[51] Int. Cl.$^5$ .......................... C12Q 1/14; C12Q 1/04; C12Q 1/06; C12R 1/46
[52] U.S. Cl. .......................... 435/36; 433/215; 433/216; 435/4; 435/29; 435/30; 435/31; 435/34; 435/36; 435/39; 435/253.4
[58] Field of Search ........... 435/4, 13, 29, 30, 31, 435/34, 36, 39, 174, 176, 253.4, 291, 292, 810, 885; 436/501; 433/215, 216

[56] References Cited

U.S. PATENT DOCUMENTS

| | | | |
|---|---|---|---|
| 2,809,149 | 10/1957 | Cusumano | 167/84 |
| 3,746,624 | 7/1973 | Hoerman et al. | 435/36 |
| 4,692,407 | 9/1987 | Jordan et al. | 435/36 |
| 4,976,951 | 12/1990 | Rosenberg et al. | 424/7.1 |

OTHER PUBLICATIONS

Newburn et al. (1984) Community Dental Oral Epidemiol., vol. 12, No. 5, pp. 325-331.
*Textbook of Microbiology* 21st Edition, by Freeman (W. S. Saunders Co., Philadelphia, USA, 1979) pp. 150-152.
*The Pharmacological Basis of Therapeutics*, 7th Edition by Goodman et al. (MacMillan Publishing Co., New York, N.Y. 1985) pp. 1193-1194.
*Physicians Desk Reference to Pharmaceutical Specialties and Biologicals* (Baker et al., Published by Medical Economics Inc. Oradell, N.J. 1972) p. 690.
*The Merck Index* (Ed., Windholz et al., 1983, Merck & Co., Inc., Rahway, N.J., USA), pp. 135 and 136.
*Bergey's Manual of Systematic Bacteriology*, vol. 2, (Ed. Sneath et al., Waverly Press, Inc., USA 1986), pp. 1054–1063.
Kohler et al. (1979), J. of Clinical Microbiology, vol. 9, No. 5, pp. 584–588.

*Primary Examiner*—Margaret Parr
*Assistant Examiner*—Ardin H. Marschel
*Attorney, Agent, or Firm*—Brumbaugh, Graves, Donohue & Raymond

[57] ABSTRACT

A method for detecting and quantifying mutans streptococci in the saliva of an individual is provided comprising the steps of (a) collecting a sample of saliva on the surface of a solid carrier strip;

(b) introducing the sample on the solid carrier strip into a liquid medium which is selective for mutans streptococci and incubating in the liquid medium for a period of time sufficient to allow growth of visible colonies of mutans streptococci; and (c) detecting and counting colonies of mutans streptococci on the surface of the solid carrier strip. The invention further provides a kit for carrying out the method of the invention. The kit includes a solid carrier strip for obtaining a sample, an incubation vessel sized to accept the solid carrier strip, and a selective medium for growth of mutans streptococci. The selective medium can be provided in a ready-to-use liquid form, in a dry form which is reconstituted with water for use, or as a number of separately packaged dry or liquid ingredients which are combined in the incubation vessel for use.

11 Claims, No Drawings

METHOD AND KIT FOR DETECTION OR QUANTIFICATION OF STREPTOCOCCUS MUTANS AND STREPTOCOCCUS SOBRINUS

This application is a continuation of application Ser. No. 07/317,624, filed on Mar. 1, 1989, now abandoned.

BACKGROUND OF THE INVENTION

This application relates to a method and kit for the detection of mutans streptococci (*S. mutans* and *S. sobrinus*) in saliva specimens.

Many papers have appeared which document the association of mutans streptococci in saliva with dental caries. See, Emilson et al. Scand. J. Dental Res. 93, 96 (1,985); W. Loesche, Microbiol. Reviews 50, 353 (1986; Van Houte et al., Proc. Int. Conf. Cellular, Molecular and Clinical Aspects of *Streptococcus mutans*, p. 157 (1986, Elsevier).

Mutans streptococci colonize the teeth, and the salivary level of mutans streptococci reflects the number of colonized sites. Emilson et al., Community Dent Oral Epidemiol 10, 111 (1982); Togelius, et al., Acta Odontol. Scand. 42, 157 (1984). Thus, the number of mutans streptococci in saliva can be used for evaluation of caries risk and is useful for monitoring the level of colonization of an individual. Zickert et al. Community Dent. Oral Epidemiol. 10, 77 (1982).

A conventional method for determining the number of mutans streptococci in a saliva sample relies on plating serial dilutions of the sample on a selective medium, incubating the samples to form colonies, counting the number of colonies formed on a manageable plate and back calculating to determine the number of viable bacteria in the original sample. This method, however, is time consuming and requires skilled and accurate handling to achieve reliable results. Further, this method is poorly suited to the development of a test kit.

Another method was described by Kohler et al., J. Clin. Microbiol 9, 584 (1979). In this method, wooden spatulas were exposed to saliva in the mouth of an individual and then placed in contact with an MSB agar surface. MSB agar is selective for growth of mutans streptococci and contains per liter: 10.0 g tryptose, 10.0 g peptone, 1.0 g dextrose, 50.0 g sucrose, 4.0 g $K_2HPO_4$, 0.075 g tryptan blue, 0.0008 g crystal violet, 15.0 g agar, 200 units bacitracin and 0.01 g potassium tellurite at a pH of 7.0. The MSB agar plates with the spatula's on the surface were incubated in plastic bags containing expired air from the individual and the number of colonies formed counted.

The Kohler "spatula" method provides a good assessment of the number of mutans streptococci in the mouth and is more convenient than direct plating of saliva samples. Nevertheless, the spatula method is not ideal, in part because of the short shelf life (about seven days) of the MSB agar plates.

It is an object of the present invention therefore to provide a test method for detecting and quantifying mutans streptococci in saliva that makes use of stable reagents that can be readily produced in kit form.

SUMMARY OF THE INVENTION

The invention provides a method for detecting and quantifying mutans streptococci in the saliva of an individual comprising the steps of (a) collecting a sample of saliva on the surface of a solid carrier strip;

(b) introducing the sample on the solid carrier strip into a liquid medium which is selective for mutans streptococci and incubating in the liquid medium for a period of time sufficient to allow growth of visible colonies of mutans streptococci; and (c) detecting and counting colonies of mutans streptococci on the surface of the solid carrier strip. The invention further provides a kit for carrying out the method of the invention. The kit includes a solid carrier strip for obtaining a sample, an incubation vessel sized to accept the solid carrier strip, and a selective medium for growth of mutans streptococci. The selective medium can be provided in a ready-to-use liquid form, in a dry form which is reconstituted with water for use, or as a number of separately packaged dry or liquid ingredients which are combined in the incubation vessel for use.

DETAILED DESCRIPTION OF THE INVENTION

The claimed invention makes use of a solid carrier strip to collect a sample of saliva and as a base for growth of colonies of mutans streptococci. In principle, any material to which the colonies will adhere can be used, for example strips made of wood or plastic. Preferred materials for the solid carrier strips are those which are also inexpensive and readily sterilized. Particularly preferred solid carrier strips are plastic strips, for example polystrene or polyacrylate, roughened on one surface to promote adherence of bacteria.

The claimed invention also makes use of a liquid growth medium which is selective for the growth of mutans streptococci. This can be accomplished by incorporating bacitracin, a broad spectrum antibacterial agent which is ineffective against mutans streptococci, into the growth medium. A preferred medium is a buffer base similar to that used in making MSB agar containing bacitracin but omitting the agar and the crystal violet. The growth medium preferably contains sucrose at a level sufficient to promote bacterial adhesion to the solid carrier strips, for example 300 g per liter. This adhesion is believed to result from the formation of a dextran bridge between the solid carrier and the bacteria.

The kit of the invention includes a solid carrier strip, advantageously sterilized and wrapped to maintain sterility; a sealable incubation vessel, for example a glass or plastic tube, and a selective growth medium. The selective growth medium, whether provided in ready-to-use liquid form or as a dry material, is advantageously provided in the incubation vessel.

In a preferred embodiment of the kit, the components of broth base for MSB agar with 30% sucrose are provided as one component of the selective medium and the bacitracin is provided separately, for example dried on a carrier such as filter paper disc. The complete selective medium is formed by introducing the paper disc to the liquid broth base just prior to use.

To test for mutans streptococci, the solid carrier strip is placed in the mouth of a test subject and rotated several times to collect a saliva sample. The solid carrier strip is then placed in an incubation vessel containing a liquid medium selective for mutans streptococci.

The vessel is then incubated for a period of time sufficient to allow the growth of visible colonies. At 37° C., the preferred incubation temperature, the incubation period is about 46 hours. Incubations at lower temperatures may require longer incubation times.

After the incubation period, the strip is removed from the liquid medium and the colonies counted. In the case that the strip used was a roughened plastic strip of dimensions 8×73 mm, and in which an 8×10 mm portion of the strip was counted, the number of colonies corresponded quite well to the number of colonies found using the spatula method. Thus, the clinical data collected to date using the spatula method can be used directly in interpreting the results of tests using the method of invention.

A further advantage of the invention lies in the stability of the dried strips after incubation. The dried colonies on the strips are stable, such that the strips can be saved, for example for comparison purposes for periods of at least a year after the sample was taken.

The method of the invention will now be further described using the following non-limiting example.

EXAMPLE

Comparison between the number of colony forming units (CFU's) of mutans streptococci obtained according to the method of the invention and the number of CFU's growing on selective agar plates, according to the spatula method (Kohler B. and Bratthall B., J. Clin. Microbiol. 9 (1979) 584).

Subject. All pupils in a school in the city of Malmo, Sweden, were included. The ages varied from 7 to 12 years with about the same number of children in each age group. A few weeks before the study, the children received a written description to be forwarded to the parents, explaining the purpose of the study. Only three children refused to participate, and one declined to give saliva, leaving 302 children in this study.

Collection of saliva. The subjects chewed a piece of paraffin wax for one minute. Then a plastic strip (8×73 mm) (Orion Diagnostica, Helsinki, Finland) which had one side roughened to favour adherence, and a wooden spatula (18×150 mm; Param Grosshandelsgesallshaft Hamburg BRD) was turned around 10 times in the mouth to be contaminated with saliva and bacteria. Any excess of saliva was removed by withdrawing the spatula between closed lips. In half the number of classes, we started with the plastic spatula, immediately followed by the wooden spatula. In the other classes, wooden spatulas were used first.

In the 61 12-year-old children, we took two consecutive plastic spatula samples either before or after the wooden spatula, followed by a paraffin stimulated saliva sample collected in a test tube. About 5 ml saliva was obtained from each child.

Incubation and counting. The plastic spatulas were immediately transferred to test tubes with 6 ml of a selective broth. The buffer base was similar to that used in MSB agar (Gold O. et al., Arch. Oral. Biol. 18 (1973) 1357) and contained bacitracin as the selective agent. To promote adhesion of colonies to the strip, 30% sucrose was added. The bacitracin solution, to select for mutans streptococci, had been prepared separately and an aliquot (30 μg) dried on small filter papers. These paper discs were added to the broth prior to use. The tubes were filled with expired air and closed with screw caps.

The wooden spatulas were pressed directly against the elevated surfaces of MSB agar in contact petri dishes (Nunc, Roskilde, Denmark) according to the original spatula method described by Kohler B. and Bratthall B., J. Clin. Microbiol. 9 (1979) 584. The plates were incubated in plastic bags containing expired air.

One ml of the saliva samples was immediately transferred to VMG transport medium (Moller A., Odontol. Tidski. 74, 1966) and then plated on MSB-agar plates (Klock B. and Krasse B., Scand. J. Dent. Res. 87 (1979) 129) within 8 hrs. These plates were incubated in 95% $N_2$, 5% $CO_2$. All tubes, NUNC-plates and regular agar plates were incubated at 37° C. for 46 hours.

After incubation, the plastic spatulas were removed from the broth and let to dry at room temperature. The number of CFU's on a predetermined area of the strip, 10×8 mm was counted under 10× magnification. Four levels were chosen for the results: 0 CFU, 1–10, 11–99 and ≧100 CFU's. The same groups were used for the spatula method. The conventional agar plates were counted and the humbler of CFU per ml saliva grouped in four groups: <104, 104–105, 105–106 and >106.

The bacterial counts obtained by the different sampling methods as well as the duplicate samples obtained using plastic strips were compared by frequency analysis using the contingency coefficient, calculated as $C = X^3/(X^3+N)$. The comparisons were all based on 4×4 groups where the maximal contingency coefficient is 0.866.

A. COMPARISON OF INVENTION WITH SPATULAS

Comparison between CFU's of mutans streptococci in saliva, obtained on the agar plates according to the spatula method and using strips according to the invention. The two samples from each subject coincided in 80% (241 cases) and 19% showed a discrepancy of one class. Total number of saliva samples is 302. Contingency is 0.78.

| Strip method, CFU | Spatula method, CFU | | | |
|---|---|---|---|---|
| | 0 | 1–10 | 11–99 | >100 |
| 0 | 87 | 14 | 2 | 1 |
| 1–10 | 1 | 18 | 14 | 0 |
| 11–99 | 0 | 9 | 54 | 7 |
| >100 | 0 | 0 | 13 | 82 |

B. REPRODUCIBILITY

Estimation of the reliability of the new method. The number of CFU's on two plastic spatulas, contaminated immediately after each other and incubated separately, were counted.

Comparison between the number of CFU's of mutans streptococci in saliva obtained on two consecutive strip mutans samples. 87% of the samples agreed and the remaining did not differ more than one class. Total number of saliva samples is 61 and contingency coefficient is 0.80.

| Strip method Sample 2, CFU | Strip mutans, Sample 1, CFU | | | |
|---|---|---|---|---|
| | 0 | 1–10 | 11–99 | >99 |
| 0 | 15 | 1 | 0 | 0 |
| 1–10 | 0 | 2 | 3 | 0 |
| 11–99 | 0 | 1 | 14 | 1 |
| >99 | 0 | 0 | 2 | 22 |

C. COMPARISON WITH CONVENTIONAL PLATING

Comparison between the mean CFU's from two plastic spatulas, with the counts of conventional plating of paraffin stimulated saliva on MSB-agar plates.

Comparison between CFU's of mutans streptococci in saliva, obtained according to the strip mutans method and conventional saliva sampling. The grouped results for the dilution-plate count method were in 77% of the subjects in accordance with the counts on the strip. A few, 16 per cent, showed higher values for the spatula and 7 percent lower. Only one sample differed by two classes. Total number of saliva samples is 60 and contingency coefficient is 0.76.

| No. of saliva samples having S. mutans (CFU:s/ml) counts | Strip mutans, CFU Mean number of two consecutive Strip method samples | | | |
|---|---|---|---|---|
| | 0 | 1–10 | 11–99 | >99 |
| <10⁴ | 14 | 3 | 0 | 0 |
| 10⁴–10⁵ | 0 | 0 | 3 | 0 |
| 10⁵–10⁶ | 1 | 0 | 13 | 4 |
| >10⁶ | 0 | 0 | 3 | 19 |

I claim:

1. A method for detecting the presence of *Streptococcus mutans* or *Streptococcus sobrinus* in saliva comprising:
   (a) collecting a saliva specimen on a solid carrier strip;
   (b) putting the strip into a complete liquid growth medium selective for growth of *Streptococcus mutans* or *Streptococcus sobrinus*, said liquid medium comprising bacitracin and an effective amount of sucrose to promote adhesion of the streptococci to the strip;
   (c) incubating the strip in the liquid medium for a period of time sufficient to allow growth of visible colonies if *Streptococcus mutans* or *Streptococcus sobrinus* are present in the specimen; and
   (d) visually checking the strip for the presence of colonies, whereby the presence of colonies is indicative of the presence of *Streptococcus mutans* or *Streptococcus sobrinus* in the sample.

2. A method according to claim 1, wherein the solid carrier strip is plastic.

3. A method for detecting and quantifying the presence of *Streptococcus mutans* or *Streptococcus sobrinus* in saliva comprising
   (a) collecting a saliva specimen on solid carrier strip;
   (b) putting the strip into a complete liquid growth medium selective for growth of mutans streptococci, said liquid medium comprising bacitracin and an effective amount of sucrose to promote adhesion of the streptococci to the strip;
   (c) incubating the strip in the liquid medium for a period of time sufficient to allow growth of visible colonies if *Streptococcus mutans* or *Streptococcus sobrinus* are present in the specimen; and
   (d) visually checking the strip for the presence of colonies and counting or estimating the number of colonies, whereby the number of colonies is indicative of the number of streptococci in the sample.

4. A method according to claim 3, wherein the solid carrier strip is plastic.

5. A method for detecting the presence of *Streptococcus mutans* or *Streptococcus sobrinus* in saliva comprising
   (a) collecting a saliva specimen on a solid carrier strip;
   (b) putting the strip into a complete liquid growth medium selective for adherent growth of *Streptococcus mutans* or *Streptococcus sobrinus* onto the strip, said liquid medium comprising bacitracin, tellurite ions and an effective amount of sucrose to promote adhesion of the streptococci onto the strip;
   (c) incubating the strip in the liquid medium for a period of time sufficient to allow growth of visible colonies onto the strip if *Streptococcus mutans* or *Streptococcus sobrinus* are present in the specimen; and
   (d) visually checking the strip for the presence of colonies, whereby the presence of colonies is indicative of the presence of *Streptococcus mutans* or *Streptococcus sobrinus* in the sample.

6. A method for detecting and quantifying the presence of *Streptococcus mutans* or *Streptococcus sobrinus* in saliva comprising
   (a) collecting a saliva specimen on a solid carrier strip;
   (b) putting the strip into a complete liquid growth medium selective for adherent growth of mutans streptococci onto the strip, said liquid medium comprising bacitracin, tellurite ions and an effective amount of sucrose to promote adhesion of the streptococci onto the strip;
   (c) incubating the strip in the liquid medium for a period of time sufficient to allow growth of visible colonies onto the strip if *Streptococcus mutans* or *Streptococcus sobrinus* are present in the specimen; and
   (d) visually checking the strip for the presence of colonies and counting or estimating the number of colonies, whereby the number of colonies is indicative of the presence of the number of streptococci in the sample.

7. A kit for the detection of *Streptococcus mutans* or *Streptococcus sobrinus* in saliva comprising;
   (a) a solid carrier strip;
   (b) an incubation vessel sized such that the solid carrier strip fits inside; and
   (c) a growth medium selective for *Streptococcus mutans* or *Streptococci sobrinus* adapted for use as a liquid, said growth medium comprising bacitracin and an effective amount of sucrose to promote adhesion of the streptococci to the strip.

8. A kit according to claim 7, wherein the growth medium is supplied in two parts, a first part comprising a nutrient broth base and a second part comprising bacitracin.

9. A kit according to claim 8, wherein the first part of the growth medium is supplied as a liquid.

10. A kit according to claim 8, wherein the bacitracin is supplied as a measured aliquot dried onto a carrier.

11. A kit according to claim 9, wherein the bacitracin is supplied as a measured aliquot dried onto a carrier.

* * * * *